(12) United States Patent
Galloway et al.

(10) Patent No.: US 9,956,745 B2
(45) Date of Patent: May 1, 2018

(54) RIGIDIZED INFLATABLE STRUCTURES

(71) Applicants: President and Fellows of Harvard College, Cambridge, MA (US); Soft Robotics, Inc., Brookline, MA (US)

(72) Inventors: Kevin C. Galloway, Somerville, MA (US); Ryan Knopf, Cambridge, MA (US); Joshua Aaron Lessing, Cambridge, MA (US)

(73) Assignees: President and Fellows of Harvard College, Cambridge, MA (US); Soft Robotics, Inc., Cambrdige, MA (US)

( * ) Notice: Subject to any disclaimer, the term of this patent is extended or adjusted under 35 U.S.C. 154(b) by 279 days.

(21) Appl. No.: 14/688,210

(22) Filed: Apr. 16, 2015

(65) Prior Publication Data

US 2015/0352813 A1 Dec. 10, 2015

Related U.S. Application Data

(60) Provisional application No. 61/980,674, filed on Apr. 17, 2014.

(51) Int. Cl.
| | |
|---|---|
| *B32B 15/08* | (2006.01) |
| *B32B 27/40* | (2006.01) |
| *A61F 5/01* | (2006.01) |
| *A61F 13/04* | (2006.01) |

(52) U.S. Cl.
CPC ............ *B32B 15/08* (2013.01); *A61F 5/012* (2013.01); *A61F 5/0102* (2013.01); *A61F 5/0106* (2013.01); *A61F 5/0118* (2013.01); *B32B 27/40* (2013.01); *A61F 13/04* (2013.01); *B32B 2307/581* (2013.01); *B32B 2535/00* (2013.01); *B32B 2571/02* (2013.01)

(58) Field of Classification Search
CPC ... B32B 15/08; B32B 27/40; B32B 2307/581; B32B 2535/00; A61F 5/0102; A61F 5/0106; A61F 5/0118; A61F 5/012; A61F 13/04
See application file for complete search history.

(56) References Cited

U.S. PATENT DOCUMENTS

| | | | |
|---|---|---|---|
| 3,901,225 A | 8/1975 | Sconce | |
| 4,391,509 A | 7/1983 | Cavagnaro | |
| 5,016,856 A | 5/1991 | Tartaglino | |
| 5,065,640 A | 11/1991 | Koren et al. | |
| 5,196,457 A | 3/1993 | Wilkinson et al. | |

(Continued)

FOREIGN PATENT DOCUMENTS

| | | |
|---|---|---|
| GB | 2296941 A | 7/1996 |
| WO | WO-2012/148472 A2 | 11/2012 |
| WO | WO-2013097127 A1 | 7/2013 |

OTHER PUBLICATIONS

International Search Report and Written Opinion dated Sep. 29, 2015, in International application No. PCT/US2015/26091, 14 pages.

*Primary Examiner* — Michael C Miggins
(74) *Attorney, Agent, or Firm* — Wilmer Cutler Pickering Hale and Dorr LLP

(57) ABSTRACT

A composite structural element is described, including: a first laminate layer comprising a plurality of first material layers; a second laminate layer comprising a plurality of second material layers; and an inflatable bladder configured for connection with a fluid inflation or deflation source and disposed in-between the first and second laminate layers.

45 Claims, 11 Drawing Sheets

(56) References Cited

U.S. PATENT DOCUMENTS

| | | | |
|---|---|---|---|
| 6,014,784 | A | 1/2000 | Taylor et al. |
| 6,161,902 | A | 12/2000 | Lieberman |
| 6,217,441 | B1 | 4/2001 | Pearman et al. |
| 8,029,263 | B1 | 10/2011 | Quenneville et al. |
| 8,469,144 | B2 | 6/2013 | Pilaar |
| 2003/0210994 | A1 | 11/2003 | Boyd |
| 2006/0260210 | A1 | 11/2006 | Tanielian et al. |
| 2009/0255841 | A1 | 10/2009 | Sanches et al. |
| 2012/0325965 | A1 | 12/2012 | Bright et al. |
| 2014/0053968 | A1 | 2/2014 | Millette et al. |

$P_{in}$   $P_{in} > P_{atm}$

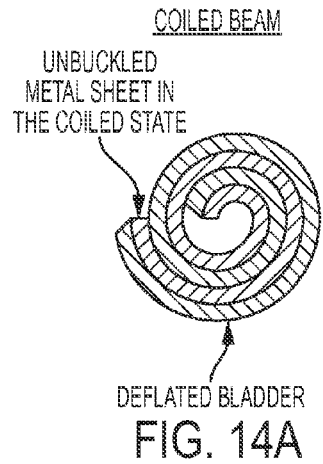
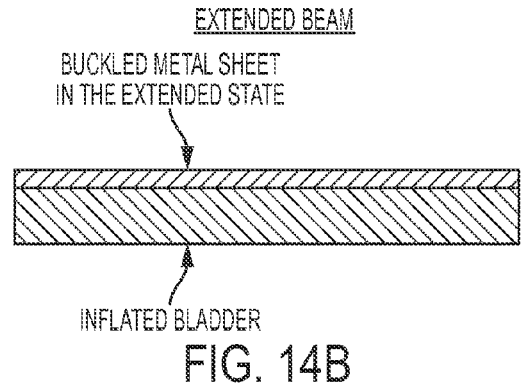
FIG. 14A
FIG. 14B
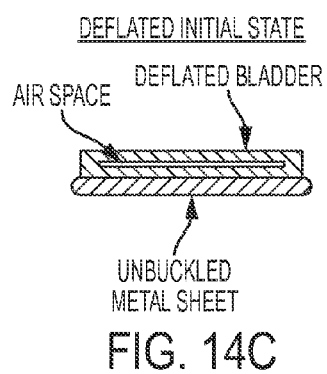
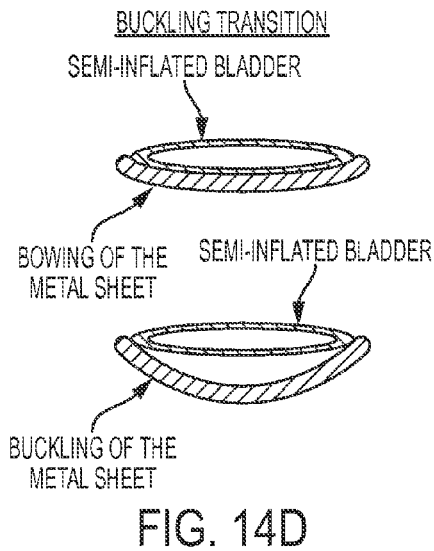
FIG. 14C
FIG. 14D
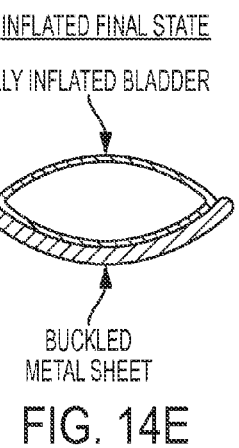
FIG. 14E

RIGIDIZED INFLATABLE STRUCTURES

RELATED APPLICATION

The present application claims priority to U.S. Provisional Application 61/980,674, filed Apr. 17, 2014, the contents of which are hereby incorporated by reference herein in their entirety.

GOVERNMENT FUNDING CLAUSE

This invention was made with support from the United States government under Grant No. N66001-13-C-4036 awarded by DARPA. The United States government has certain rights to this invention.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

Field of the Invention

The present disclosure generally relates to the field of rigidized structures. In particular, the disclosure relates to structures that are flexible in their inactive state, and stiffen when activated. Structures that are permanently rigid—for the purposes of illustration consider a long pole—can be awkward to transport and can be difficult to deploy in constrained spaces. The capacity for a structure to shift from a flexible state to a rigid state is advantageous where portability and/or navigating tight space constraints are important. For example, in a flexible state, a structure can be configured to a shape that is more convenient for transport and then deployed when needed. In constrained spaces, a structure in a flexible state can be configured to navigate around obstacles and then be activated to provide support.

SUMMARY

Described herein is composite structural element that is flexible in its inactive state, which is also referred to as the "resting" state (state 1, or resting state 1) throughout this application, and stiffen when activated, which is also referred to as the "active" state (state 2, or active state 2).

In one aspect, a composite structural element, including: a first laminate layer comprising a plurality of first material layers; a second laminate layer comprising a plurality of second material layers; and an inflatable bladder configured for connection with a material infusion or vacuum source and disposed in-between the first and second laminate layers, wherein the composite structural element is configured to rigidize when the bladder is inflated.

In one or more embodiments, a composite structural element demonstrating greater strength and rigidity in its activated state is achieved using an inflatable bladder or balloon to reversibly space apart laminate layers. As used herein, the term "bladder" refers to any inflatable, enclosed structure which is configured for connection with a fluid inflation or deflation source, and in which the bladder interior can be isolated from the outside atmosphere. In a resting state 1, the bladder is deflated and the laminate layers are positioned close to one another. If the laminate layers are themselves flexible, the overall structure in its resting state will be flexible. In the activated state 2, the bladder is inflated to space apart the laminate layers and maintain the spacing between the two laminate layers. The increase in distance between the laminate layers and its centroidal axis increases the structural stiffness.

In other embodiments, the second moment of area of a beam can be adjusted by changing the effective thickness, h. This can have a powerful effect on the stiffness of a beam. One non-limiting example is to have several thin material layers stacked on top of each other. If they are allowed to slide past one another, the second moment of area is the product of n, the number of beams, where the second moment of area for a single beam is $I=(nbh^3)/2$. However, if there is adhesion between the material layers (either through glue, interlocking physical features, friction, etc) the layers behave more as a single beam, which brings n inside the cubed term, $I=b(n*h)^3/2$. This dramatically changes the stiffness of the beam. Thus, in certain embodiments, the first or second material layers have patterned surfaces (toothed, ridged, pegged, hooked, diamond cut, etc) to create a mechanically interlocked bond between laminates in state 2.

In one aspect, a composite structural element is described, including:
a first laminate layer comprising a plurality of first material layers;
a second laminate layer comprising a plurality of second material layers; and
an inflatable bladder configured for connection with a material infusion or vacuum source and disposed between the first and second laminate layers; wherein the composite structural element is configured to rigidize when the bladder is inflated.

In any one of embodiments described herein, each of the first material layers is made from a material the same as any other first material layers or different from at least one other first material layer.

In any one of embodiments described herein, each of the second material layers is made from a material the same as any other second material layers or different from at least one other second material layer.

In any one of embodiments described herein, the bladder has a membrane and the first and/or second material layers adjacent to the bladder are bounded to the bladder's membrane.

In any one of embodiments described herein, one of the first material layers and one of the second material layers are sealed together to form the membrane of the bladder.

In any one of embodiments described herein, the first and second laminate layers are configured to become more rigid when the bladder is pressurized.

In any one of embodiments described herein, the first and/or second laminate layers are configured to curve when the bladder is pressured.

In any one of embodiments described herein, the distance between the first and second laminate layers is configured to increase when the bladder is pressurized.

In any one of embodiments described herein, the distance between the first and second laminate layers is configured to increase and the first and/or second laminate layers are configured to curve when the bladder is pressured.

In any one of embodiments described herein, the first and second laminate layers each independently comprise 2, 3, 4, 5, 6, 7, or more first or second material layers, respectively.

In any one of embodiments described herein, the space between the first material layers or the second material layers is configured for connection with a vacuum source.

In any one of embodiments described herein, the facing surfaces of the two adjacent first material layers or the two adjacent second material layers are textured to create high friction between the first material layers or between the second material layers, respectively, when the bladder is inflated.

In any one of embodiments described herein, the first or second material layers are rubberized to create high friction between the material layers when the bladder is infused.

In any one of embodiments described herein, the two adjacent first or second material layers have patterned surfaces to create a mechanically interlocked bond between laminates when the bladder is infused.

In any one of embodiments described herein, the two facing surfaces of the adjacent first material layers or the adjacent second material layers each comprises a set of opposing ratcheting teeth configured to interlock to impart directional bending effects after the bladder is infused.

In any one of embodiments described herein, the two adjacent first or second material layers are bounded together.

In any one of embodiments described herein, the two adjacent first material layers or the second material layers freely slide pass one another.

In any one of embodiments described herein, the composite structural element is configured to de-rigidize when the bladder is deflated.

In any one of embodiments described herein, the composite structural element permanently rigidizes when the bladder is inflated.

In any one of embodiments described herein, at least one material layer comprises polymerizable monomers susceptible to UV polymerization.

In any one of embodiments described herein, the bladder is configured for connection with a resin infusion source or a foam inflation source.

In any one of embodiments described herein, the material layer comprises pre-preg composite materials configured to be cured through chemical, radiant, or electrical means.

In any one of embodiments described herein, the first or second laminate layer comprises integrated electronic circuitry.

In any one of embodiments described herein, at least one of the first and second laminate layers is housed in a sleeve.

In any one of embodiments described herein, the first and/or second laminate layers are sealed in the sleeve and the sleeve is configured for connection with a vacuum resin infusion system.

In any one of embodiments described herein, the first and/or second laminate layers are sealed in the sleeve and the sleeve is configured for connection with a vacuum source.

In any one of embodiments described herein, the bladder is configured to be infused before the sealed sleeve is subjected to the vacuum.

In any one of embodiments described herein, both the first and second laminate layers and the bladder are housed in a sleeve.

In any one of embodiments described herein, the composite structural element is capable of being rolled or folded.

In any one of embodiments described herein, the bladder houses one or more system components.

In any one of embodiments described herein, the system component is a soft actuator.

In any one of embodiments described herein, the composite structural element further includes one or more internal reinforcement in the bladder configured to adjust the separation distance between the first and the second laminate layers.

In any one of embodiments described herein, the separation distance may be adjusted actively or passively.

In any one of embodiments described herein, the composite structural element comprises a plurality of the reinforcements configured to be independently adjusted or adjusted as a group.

In any one of embodiments described herein, the first and/or second material layer further comprises one or more openings configured to allow viewing access into the bladder.

In any one of embodiments described herein, the first and/or second material layer further comprises one or more openings passing through the bladder and the first and/or second material layer.

In any one of embodiments described herein, the opening is configured to house one or more additional system components or materials.

In any one of embodiments described herein, the composite structural element has a tapered geometry.

In any one of embodiments described herein, the first or second laminate layers are made from puncture-resistant and/or bulletproof materials.

In any one of embodiments described herein, at least one of the first and second laminate layers is housed in a sleeve containing shear thickening fluids.

In any one of embodiments described herein, the structural element has a rigid body when the bladder is infused.

In another aspect, a composite structural element array is described, including two or more composite structural elements each according to any of the embodiments described herein, combined or connected, reversibly or irreversibly in series, parallel, or at an angle.

In any one of embodiments described herein, each of the composite structural elements is connected to the same material infusion or vacuum source.

In any one of embodiments described herein, at least two of the composite structural elements are connected to different material infusion or vacuum sources.

In yet another aspect, a device including a composite structural element of any one of the embodiments described here is disclosed, wherein the device is selected from the group consisting of a splint, a wing structure, a load bearing scaffold, a shelter, a bullet proof structure, a communication tower, bridge and a truss.

In any one of embodiments described herein, the splint is a splint for wrist, arm, leg, or femur.

It is contemplated that any embodiment disclosed herein may be properly combined with any other embodiment disclosed herein. The combination of any two or more embodiments disclosed herein is expressly contemplated.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "linked to," "on," "connected to," "coupled to," "in contact with," etc., another element, it may be directly linked to, on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

DESCRIPTION OF THE DRAWINGS

The following images also detail multiple applications and features that can be incorporated into the structures. In these examples, we assume there is a connection to a pressurized fluid source. The invention is described with reference to the following figures, which are presented for the purpose of illustration only and are not intended to be limiting. In the Drawings:

FIGS. 14A-E: Present several views of a pressurized bladder that can drive a metal sheet from a coiled state to a linear beam, accordingly to one or more embodiments. FIG. 14A is a side view of the device in its coiled state before pneumatic actuation. FIG. 14B is a side view of the device in its inflated state. FIG. 14C shows a cross-section view of the device, taken perpendicular to its length, before inflation. FIG. 14D shows that the bladder is inflated which initially bows the metal sheet until the sheet is driven through a buckling transition. FIG. 14E shows that the bladder is further inflated to provide additional rigidity to the bean.

DETAILED DESCRIPTION

Figure 1A:
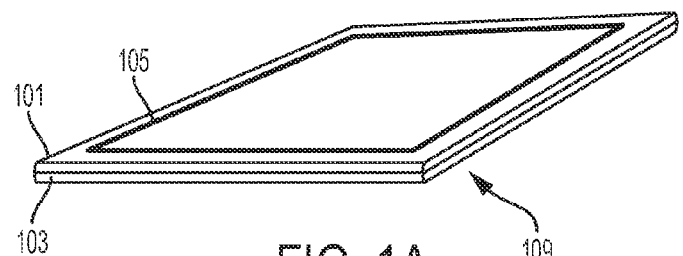
FIG. 1A: Shows the perspective view of an inflatable bladder including two sheets that are sealed along the perimeter, accordingly to one or more embodiments.

The present disclosure identifies several techniques for altering the second moment of area of a structure in order to affect the overall stiffness of a structural element including flexible laminate material layers. "Second moment of area," as used herein, is a measure of the 'efficiency' of a shape to resist bending caused by loading where a shape with a higher second of moment is more resistant to bending. The stiffness of a beam, k, is proportional to the product of the Young's modulus of the material, E, and the second moment of area, I. That is $k \propto EI$. The second moment of area of a beam with a rectangular cross section is calculated at $I=1/2bh^3$, where b is the width, and h is the thickness. Curving the cross section of the beam to form an arc shape can significantly increase the I value and therefore increase the stiffness of the beam (or its resistance to bending). For example, a beam that has a height of 0.0625" and a width of 2" has an I value of $2.4 \times 10^{-4}$ inches$^4$. However, by curving the beam slightly to achieve a 1.30" outer radius, R, (which results in a 1.24" inner radius, r), the second moment of area increases in value by a factor of 10 to $2.4 \times 10^{-3}$ inches$^4$ (note the governing equation for the second moment of area of a beam with a curved cross section is $$0.1098(R^4 - r^4) - \frac{0.283 R^2 r^2 (R-r)}{R+r}).$$

The second moment of area can also be adjusted by increasing the distance between two or more laminate layers and their centroidal axis (known as the parallel-axis theorem), which is defined as $I_x = I_{cg} + Ad^2$, where $I_{cg}$ is the second moment of area of the beam about its center of gravity (e.g. $I=1/2bh^3$), A is the cross-sectional area of the beam, and d is the distance from any parallel axis.

In one aspect, a composite structural element is described, including: a first laminate layer comprising a plurality of first material layers; a second laminate layer comprising a plurality of second material layers; and an inflatable bladder configured for connection with a material infusion or vacuum source and disposed in-between the first and second laminate layers. As used herein, "laminate" or "laminate layer" refers to a structural element which include more than one material layers. As used herein, "laminate layer" may be also be referred to as "rigidizing element" or "rigidizing beam." As used herein, "material layer" refers to any single structural layer made of flexible or rigid material. As described herein, the laminate layers and, in turn, the composite structural element, have two states: a first non-rigid or less rigid state (also referred to as state 1 or non-activated state) and second rigid or rigidized state (also referred to as state 2 or activated state) which is more rigid than the first state. The first and second laminate layers are each independently flexible (non-activated state) when the bladder is not pressurized and become more rigid (activated state) and rigid when the bladder is pressurized.

In certain embodiments, the first or second laminate layers are puncture-resistant or bulletproof when the bladder is infused.

The composite structural element can be constructed in many ways so that the bladder is disposed between the first and second laminate layers. In some embodiments, the first and second laminate layers surround the bladder, which has its independent membrane defining the bladder. In some specific embodiments, the first and second laminate layers are adhered to opposing surfaces, e.g., membranes, of the bladder. In other embodiments, one of the first material layers and one of the second material layers are sealed together to serve as the membrane to form the bladder.

The bladder is configured for connection with a material infusion or vacuum source. In some embodiments, the material infusion or vacuum source is a fluid inflation or deflation source. The bladder may be inflated or pressurized by gas, fluid, or any other pressurizing means known in the art. Thus, in certain embodiments, the pressure inside the bladder is greater than the pressure outside the bladder as a result of the bladder pressurization, and the first or second laminate layer surrounding the bladder will change shape, e.g., curve, to accommodate the pressure and/or change volume and thereby increase the separation distance between layers. Consequently, the stiffness of the laminate layer, and in turn the stiffness of the composite structural element, is greatly increased. This change of the stiffness of the laminate may be referred to as rigidizing. The rigidized first or second laminate layer as well as the composite structural element can be used for structural support in applications such as splinting, structural component, construction, packaging, due to their greatly increased stiffness.

In some embodiments, the composite structural element is rigidized by material infusion, e.g., fluid pressurization, into a bladder to change from state 1 to state 2 and vice versa. In certain specific embodiments, the material infusion or vacuum source is a fluid inflation or deflation source, which is optionally external to the composite structural element, and can be any apparatus which inflates and/or deflates the fluid. Non-limiting example of the fluid inflation or deflation sources include a gas pump, a gas vacuum, a gas pump and vacuum, a liquid pump, a liquid-suction pump, or a liquid pump and suction. The use of any fluid, gas or liquid, is contemplated, including air, gas, water, oil, liquid, and metal. A non-limiting example of the gas is air. The use of other gases is contemplated. In other embodiments, the material infusion source also includes a resin infusion source or a foam infusion source. Thus, the term "infusion," as used herein, includes not only fluid pressurization (gas or liquid) but also foam or resin infusion. However, it will be evident that other approaches could be used including electrostatics, electroactive polymers, motors with cables, hand wound clutches with cables, and so forth.

In some embodiments, the first or second laminate layer comprises two or more material layers each independently made of a material which, when curved, results in an increased stiffness. In some embodiments, on each side of the bladder, the first and/or second laminate layers include more than 2, 3, 4, 5, 6, 7, 8, 9, 10, 15, 20, 25, 30, 40, 50, or 100 material layers, or in the range of 2 to 100 layers, or any other range bounded by any of the values noted here. Non-limiting examples of the material for the material layers include metal, fiberglass, paper, composite wood, and plastic. Each material layer of the first and second laminate layers is made from a material independent of the material of the other material layers, that is, each of the first material layers can be made from the same material as any other material layer or different from at least one other material layer. In some embodiments, one or more of the material layers are thin and has a thickness of less than 10 cm, 5 cm, 4 cm, 3 cm, 2 cm, 1 cm, 500 µm, 400 µm, 300 µm, 200 µm, 100 µm, 50 µm, 10 µm, 1 µm, 500 nm, 400 nm, 300 nm, 200 nm, or 100 nm, or in the range of 100 nm to 10 cm, or any other range bounded by any of the values noted here. In some embodiments, the increased stiffness of the composite structural element may be a combination of the pressure inside the bladder and the increased stiffness of the laminate layer due to its shape change, e.g., curving or grouping of laminate layers. In certain embodiments, the increased stiffness of the composite structural element is predominantly a result of the shape change of the first and/or second laminate layer. In certain embodiments, the stiffness increase of the first and/or second laminate layer due to curving contributes to more than about 99%, 95%, 90%, 80%, 70%, 60%, or 50% of the rigidity of the composite structural element after it is rigidized. Thus, in some embodiments, the pressure increase inside the bladder does not make a significant contribution (e.g., less than 15%, 10%, 5% 3%, 2%, or 1%) to the rigidity of the composite structural element.

In certain embodiments, the composite structural element is configured to rigidize when the bladder is inflated and de-rigidize, i.e., return to its flexible state, when the bladder is deflated. In other embodiments, the composite structural element is configured to permanently rigidize when the bladder is inflated. In these embodiments, the rigidization is irreversible. In certain embodiments, UV polymerization or heat is used to permanently rigidize the laminate layers. For example, laminate layers could contain a polymer such that when UV or heat is applied to polymer cures and acts as a matrix to stiffen the bond and stiffen the laminate layers. curable polymer. In other embodiments, vacuum resin infusion can be used to encapsulate the laminate layers in an epoxy matrix to permanently rigidize the laminate layers. In other embodiments, the laminate layers could consist of thermoplastic materials which have the property that their shape can be altered with heat. Thus, inflation of the bladder combined with an external or internal heat source can alter the resting shape of the laminate layers (e.g. the laminate layers may take on a curved shape when the bladder is deflated). In still other embodiments, an expanding foam can be mixed and injected into the bladder via application of pressure to permanently rigidize the structural element and maintain its inflated form. In still other embodiments, the material layer comprises pre-preg composite materials which may be internally or externally cured through chemical, radiant, or electrical means.

In certain embodiments, the material layers in laminate layers are completely separable from one another or can freely pass one another. In other embodiments, the two adjacent material layers are bounded together or contain contacting surfaces with high friction. For instance, the two adjacent material layers can be rubberized to create high friction between the material layers when the bladder is infused. Alternatively, the two adjacent material layers can be mechanically interlocked when the bladder is infused. In certain embodiments, the two adjacent material layers' facing surfaces are regularly patterned (toothed, ridged, pegged, hooked, diamond cut, etc) to create a mechanically interlocked bond between laminates in state 2.

In other embodiments the laminate layers can be a pocket, bag or container. The pocket, bag or container can include multiple material layers enclosed in a wrapping or pocket. See, e.g., FIG. 5A-5F.

In some embodiments, shear thickening fluids (STF) can be used to occupy the space inside of a pocket, wrapping or container that houses the laminate layer. The shear thickening fluids can be used in combination with or in place of the laminates. STF's act like solids with dynamic impacts, but behave like a viscous liquid when constant force is applied. This gives the composite structural element force-time dependent rigidity. For example, if one were to apply an impulse force (e.g., a hit) to this arrangement, the object would feel very rigid. However, if the user slowly applied a force, the object would be deformable. Thus, in certain embodiments, the rigidized structural element exhibits force-time dependent rigidity.

Figure 1B:
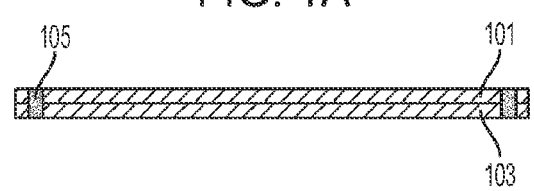
FIG. 1B: Shows a cross-section view of the inflatable bladder in state 1 (i.e. not pressurized), accordingly to one or more embodiments.
Figure 1C:
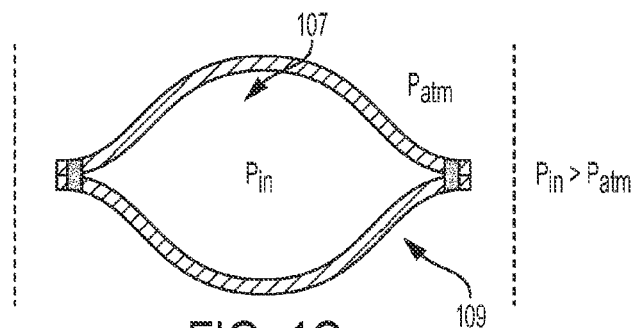
FIG. 1C: Depicts a cross-section view of the inflatable bladder in state 2 (i.e. pressurized), accordingly to one or more embodiments.

FIG. 1A shows a composite structural element 109 according to one or more embodiments including an inflatable bladder formed between first and second laminate layers, 101 and 103, respectively, that are sealed along the perimeter 105. In this construct, the laminate layers, taken together, also forms the bladder in-between the first and second laminate layers 101 and 103. A cross section view of this composite structural element is shown in FIG. 1B (shown in the non-activated state). Note that the first and second laminate layers 101 and 103 may each include a plurality of material layers (not shown). As shown in FIG. 1C, when the bladder 107 is pressurized to state 2 (activated state) such that the pressure inside ($P_{in}$) is greater than the atmospheric pressure outside the bladder ($P_{atm}$), the element 109 forms a rounded cross section. For the circular cross section to form, $P_{in}$ only needs to be slightly greater than $P_{atm}$. In some embodiments, $P_{in}$ is about 1, 2, 3, 4, 5, 6, 7, 8, 9, 10, 15, 20, 25, 30, 40, 50, 100, or 1000 psi greater than $P_{atm}$, or in the range of 1 to 500 psi greater than $P_{atm}$, or any other range bounded by any of the values noted here. This curving of the laminate layers alone greatly increases the second moment of area of the two laminate layers to make a stiffer structural element.

Figure 2A:
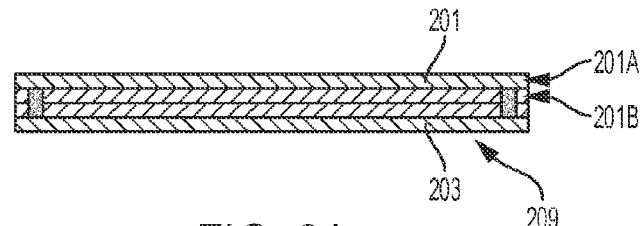
FIG. 2A: Depicts a cross-section view of the inflatable bladder with flexible material layers bonded to the inflatable bladder, accordingly to one or more embodiments.
Figure 2B:
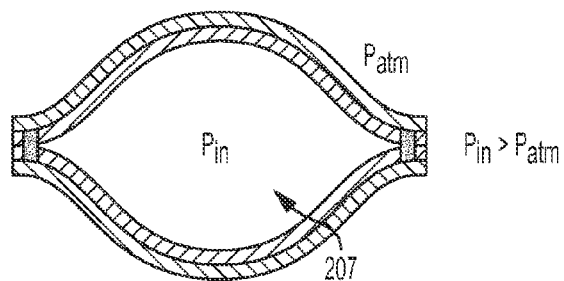
FIG. 2B: Depicts a cross-section view of the inflatable bladder in state 2 with flexible material layers matching the curvature of the bladder and thereby increasing the stiffness of the beam, accordingly to one or more embodiments.

As described herein, the stiffness of the composite structural element can be further increased by multiple material layers. One exemplary embodiment is shown in FIG. 2A, which shows a composite structural element 209 that includes first and second laminate layers 201 and 203 on each side of the bladder 207 (FIG. 2B) and each comprising 2 material layers (for instance, laminate layer 201 contains material layers 201A and 201B). Thus, the stiffness of this structure is further increased by bonding multiple material layers to create flexible laminates 201 and 203. As shown in FIG. 2B, when the bladder is pressurized to state 2 (i.e., $P_{in} > P_{atm}$), layers 201 and 203 will deform to a form a curved cross-section, which will significantly increase the stiffness of the beam. Specifically, as explained herein, if the multiple material layers on each side of the structure are allowed to slide past one another, the second moment of area is the product of n, the number of the material layers, and the second moment of area for a single material (e.g., a beam), $I=(nbh^3)/2$. However, if there is adhesion between the material layers (either through glue, vacuum, interlocking physical features, friction, etc, not shown in FIG. 2B), the material layers behave more as a single beam or single laminate layer, and the equation governing the second moment of area of the beam becomes $I=b(n*h)^3/2$. This dramatically changes the stiffness of the beam.

In some embodiments, materials that are flexible (e.g. thin fiberglass, paper, thin metal, plastic, etc) can be used for the material layers. These materials may also have other desirable properties such as high tear, cut, or puncture resistance.

Figure 3A:
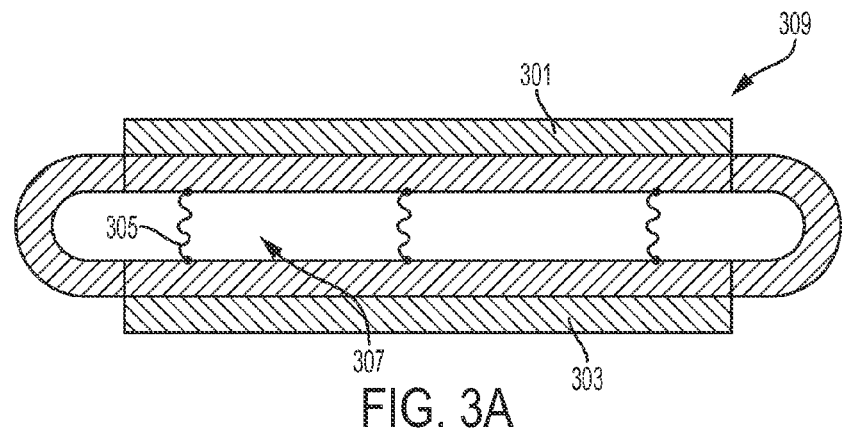
FIG. 3A: Presents a cross-section view of a rigidizing beam that increases the separation of the material layers to increase the second moment of area, accordingly to one or more embodiments.

In some embodiments, the second moment of area of two laminate layers is increased by increasing the distance between the two laminate layers. FIG. 3A illustrates a cross-section view of a composite structural element 309 that increases the separation of laminate layers 301 and 303 to increase the second moment of area. Laminate layers 301 and 303 each comprise flexible or rigid material layers. In some embodiments, the structural element 309 further includes internal reinforcements 305 restricting the spacing of the laminate layers. The governing equation for second moment of area of this construct is $I=3h/(2bt)$, where t is the thickness of the laminate, b is the width, and h is the separation distance between laminate layers.

Figure 3B:
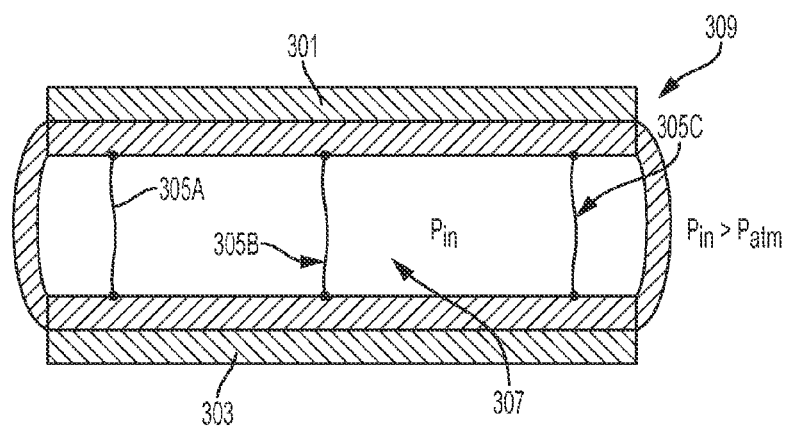
FIG. 3B: Depicts the cross-section view of the beam in state 2, where the distance between material layers is constrained by internal reinforcements, accordingly to one or more embodiments.

Once the bladder 307 of the structural element 309 in FIG. 3A is pressurized (i.e., $P_{in} > P_{atm}$), FIG. 3B illustrates the cross section view of the pressurized structure where the distance between layers 301 and 303 increases (thereby increasing the stiffness of the structural element 309). In certain embodiments, the internal reinforcements 305A-C limit the separation of the layers 301 and 303 (shown in FIG. 3B). Thus, the reinforcements may be adjusted independently or adjusted as a group.

Figure 3C:
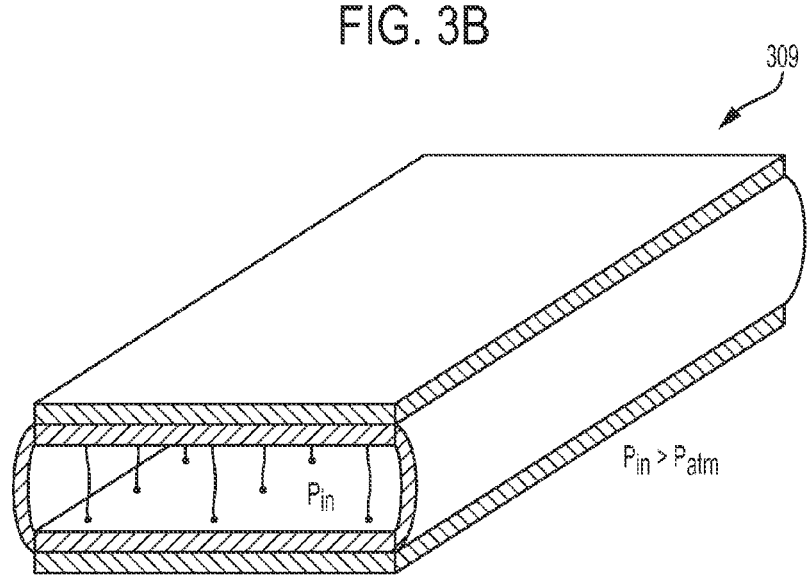
FIG. 3C: Depicts an isometric cross-section view of the rigidizing beam in state 2, accordingly to one or more embodiments.

In some embodiments, the internal reinforcements can be used to limit the curvature of the device. For example, in some embodiments, one of the reinforcements, e.g., the middle reinforcement 305B (FIG. 3B), could be longer than the two neighboring reinforcements 305A and 305C, which would permit curvature to layers 301 and 303 in addition to the increase in separation distance. Thus, when at least one of the reinforcements is of a length different from the other two reinforcements, various curvatures can be obtained. FIG. 3C depicts an perspective view of the pressurized composite structural element 309.

Figure 4A:
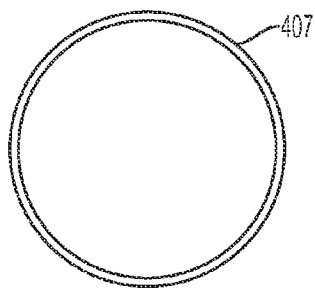
FIG. 4A: Presents a cross-section view of an inflatable bladder that is tubular, accordingly to one or more embodiments.
Figure 4B:
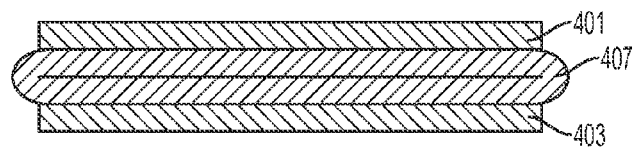
FIG. 4B: Presents a cross-section view of a tubular bladder in state 1, with flexible material layers bonded to the wall of the bladder, accordingly to one or more embodiments.
Figure 4C:
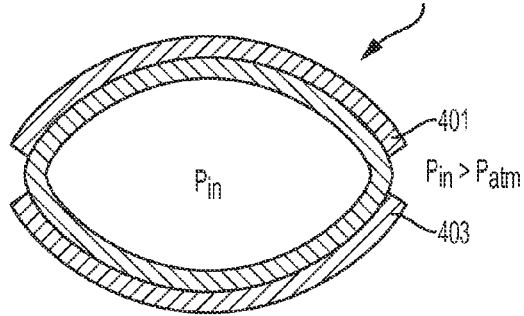
FIG. 4C: Presents a cross-section view of the tubular bladder in state 2, with flexible material layers matching the curvature of the bladder thereby increasing the stiffness of the tube, accordingly to one or more embodiments.

In other embodiments, rather than joining two laminate layers to form the bladder (e.g., FIGS. 1 and 2), a separate bladder can be used. For example, the bladder can be a tubular bladder. FIG. 4A shows a cross-section view of an inflatable, tubular bladder 407. The composite structural element 409 includes the tubular bladder 407 and two optionally flexile laminate layers, e.g., first and second laminate layers 401 and 403, attached to the wall of the bladder 407 on both sides (FIG. 4B). Each of the laminate layers may comprise two or more material layers. Alternatively, 401 and 403 can each be a single material layer and, together with the membrane layer of the bladder, form the laminate layers. The tubular bladder 407 can then be pressurized (i.e., $P_m > P_{atm}$), causing laminate layers 401 and 403 to curve to increase the stiffness of the structure 409 (FIG. 4C).

Figure 4D:
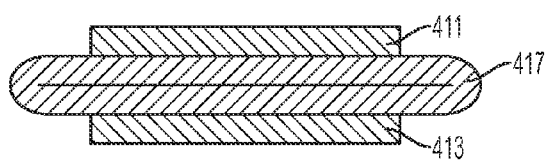
FIG. 4D: Presents a cross-section view of the tubular bladder in state 1, with material layers narrower than the diameter of the tube, and internal reinforcements (not shown), accordingly to one or more embodiments.
Figure 4E:
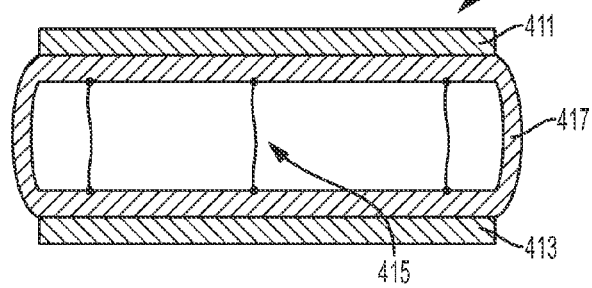
FIG. 4E: Depicts a cross-section view of the tubular bladder in state 2, where the distance between material layers is constrained by internal reinforcements, accordingly to one or more embodiments.

Alternatively, the composite structural element 419 can include tubular bladder 417 and laminate layers 411 and 413 which are narrower than the diameter of the tube attached to both sides of the tubular bladder 417 (FIG. 4D). Optionally, internal reinforcements 415 (not shown in FIG. 4D; shown in FIG. 4E) can be included to adjust the distance between the two laminate layers 411 and 413. In these embodiments, the laminate layers 411 and 413 can be made of flexible materials (e.g. thin fiberglass or carbon fiber, thin metals, thin plastic, thin fibrous materials such as paper, etc.,) or rigid materials (e.g. thick fiberglass or thick carbon fiber, thick metals, thick plastic, thick fibrous materials such as wood, and etc). FIG. 4E shows the bladder 417 pressurized. It should be noted that the diameter of the tube in this arrangement can be increased to increase the separation distance between layers 411 and 413, and thus increase the second moment of area to increase the stiffness of the structure 419. In certain embodiments, when rigid material layers are used for the laminate layers, the separation distance between the layers is determined by the cross-sectional length of tube that is not covered by the rigid materials, i.e., $$\text{Distance between layers} = \frac{(\text{tube circumference}) - (\text{layer 1 width}) - (\text{layer 2 width})}{2}$$

Figure 5A:
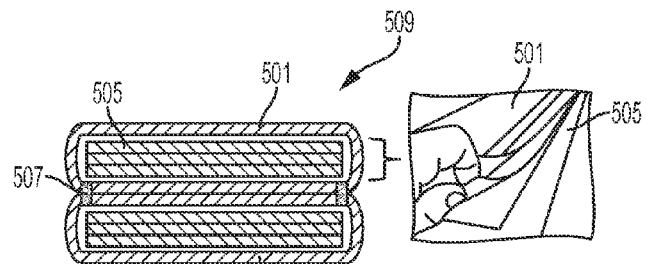
FIG. 5A: Depicts a cross-section view of a rigidizing beam in state 1 that incorporates multiple layers or laminates, accordingly to one or more embodiments.

FIG. 5A shows a rigidizing composite structural element 509 that incorporates multiple (e.g., 3) laminate layers 505 in each of pockets 501 and 503, which are sealed together at the two contact points 507 shown to form a bladder (508 shown in FIG. 5C) in between the two pockets. FIG. 5A, at right, shows the sheets 505 and the pocket 501 used for assembly of laminate layer. When the device is in state 1 (the less rigid state), these layers 505 can slide past one another to give the structure flexible properties.

Figure 5B:
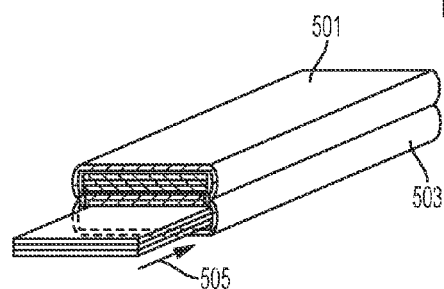
FIG. 5B: Presents an isometric view of pockets adjacent to a bladder and can accept multiple laminates, accordingly to one or more embodiments.

FIG. 5B shows the two pockets 501 and 503 that are stacked to and sealed to form the bladder. The pockets can accept multiple laminates 505, which can be inserted into the pockets as shown by the arrow. The laminate sheets can be introduced before or after sealing pockets 501 and 503. Alternatively, the laminates can be positioned over the bladder and sealed in place.

Figure 5C:
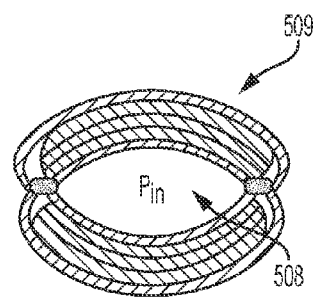
FIG. 5C: Depicts the bladder in state 2 with laminate layers matching the curvature of the bladder, accordingly to one or more embodiments.

FIG. 5C illustrates the composite structural element 509 in state 2 (rigidized state, i.e., $P_{in} > P_{atm}$) which causes the laminate layers 505 to curve. In some embodiments, the laminate layers can be sealed in the pockets and a vacuum applied to the volume inside the pockets to increase the normal force between the layers and minimize the ability of these layers to slide past one another.

The laminate layers could also have textured surfaces that minimize slip between layers when the device is pressurized, thus further causing them to behave as a single layer rather than multiple layers. Furthermore, these laminates or layers can be constructed from materials that achieve dual functions. For example, they can be made of flexible or rigid circuit boards and used to change the second moment of area of the system as well as incorporate sensors, batteries, lights, microprocessors, and so forth.

In some embodiments, the laminate layer has a high aspect ratio. As used herein, aspect ratio refers to the ratios of the long dimension to the short dimension of an object or particles. An aspect ratio of more than one is generally referred to as high aspect ratios. In certain embodiments, the laminate layer has an aspect ratio of more than 1:1, 2:1, 3:1, 4:1, 5:1, 10:1, or 20:1, or in the range denoted by any two values described herein. Other suitable high aspect ratios are contemplated. In certain embodiments, laminate layer with a high aspect ratio is a beam.

As described herein, the aspect ratio of the cell may also contribute to the predetermined actuation pattern. A non-limiting example is described earlier and in FIGS. 1f) and 1g), where the cell has an eclipse shape and thus the cell will collapse along its shorter axis when the cell is deflated.

Figure 5D:
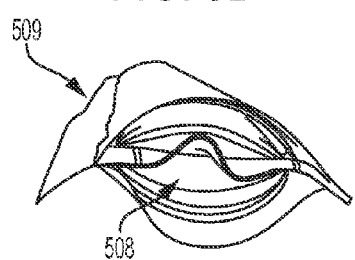
FIG. 5D: Presents an end view of a physical embodiment of FIG. 5C, accordingly to one or more embodiments.
Figure 5E:
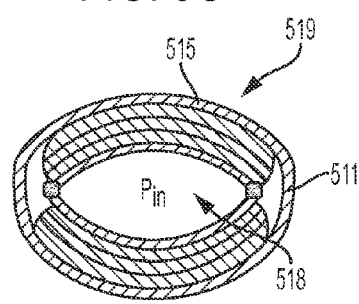
FIG. 5E: Presents a cross-section view of a single sleeve containing the laminates and bladder, accordingly to one or more embodiments.
Figure 5F:
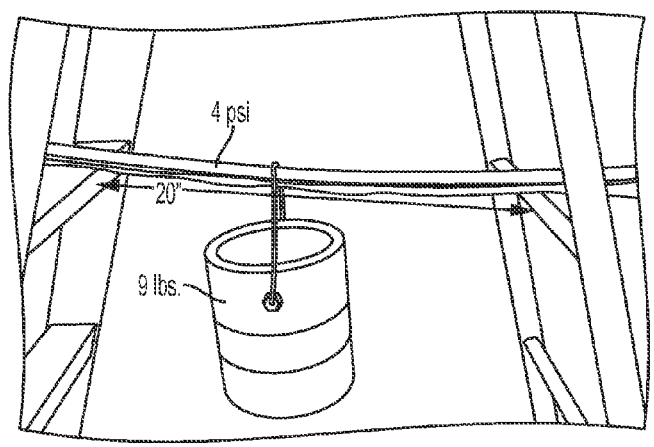
FIG. 5F: Presents a physical embodiment of FIG. 5C, pressurized to 4 psi and subjected to a three point bending test, accordingly to one or more embodiments.

FIG. 5D illustrates an embodiment of FIG. 5C reduced to practice, which shows the composite structural element 509 in state 2. The example has three laminate layers made of fiberglass with a flame-retardant resin (aka FR4) with 80 grit sandpaper bonded between the laminate layers to increase friction between layers. These laminate layers are positioned on each side of the pressurized bladder by sealing the contact points of the two pockets stacked together. The bladder in this embodiment is fabricated using 11 mil thick thermoplastic polyurethane film, but other materials such as PVC, HDPE, LPDE, nylon, and etc. could be used. FIG. 5E illustrates an alternative embodiment of the composite structural element 519 wherein the laminates 515 and bladder 518 are contained in a single sleeve 511. The pressurization of the bladder 518 into sleeve 511 has the effect of increasing the normal force (which is a function of the pressure differential between the $P_{in}$ and $P_{atm}$) between the laminate layers 505 thereby increasing the bond between them and causing them to behave as a single layer rather than multiple laminate layers. FIG. 5F shows a physical embodiment of the structure 509 described in FIG. 5A that has been pressurized to 4 psi (i.e., $P_{in}-P_{atm}=4$ psi). In a simple three point bending test, this structure is capable of supporting a 9 pound payload near the mid-point, which illustrates greatly increased stiffness of the structure. In these embodiments, the increased stiffness of the laminate layers and the pressure inside the bladder contribute to the rigidity of the composite structural element.

Figure 6A:
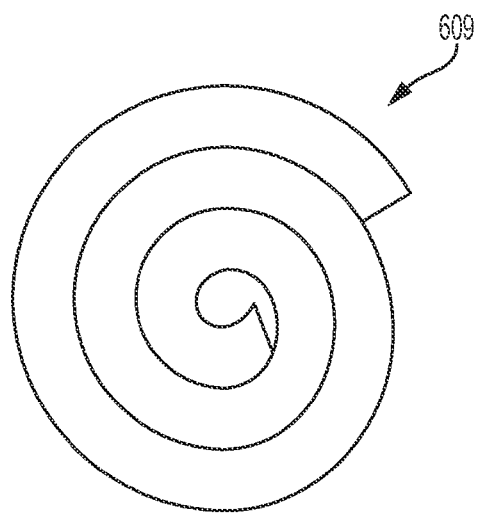
FIG. 6A: Illustrates a side view of the rigidizing beam in state 1 where it can be rolled into a compact shape, accordingly to one or more embodiments.
Figure 6B:
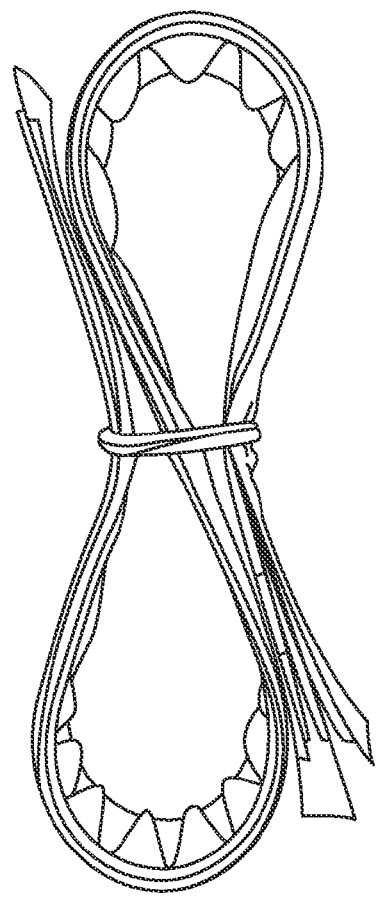
FIG. 6B: Presents a physical embodiment of a rigidizing beam in state 1, folded into a compact shape, accordingly to one or more embodiments.

In one or more embodiments the composite element in its resting state can be flexible. Thus, it can be rolled or shaped into a compact form. By way of illustration, FIG. 6A demonstrates that in state 1 (the less rigid or flexible state), the composite structural element 609 can be flexible and rolled into a compact shape. For instance, FIG. 6B demonstrates that the physical prototype of the structural element (in state 1), which includes laminate layers made of FR4, can be folded into a compact shape.

Figure 7:
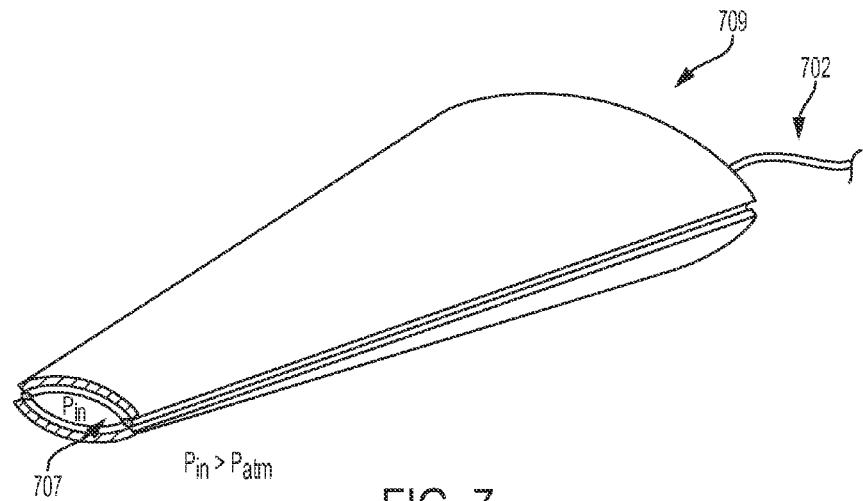
FIG. 7: Illustrates an isometric view of a rigidizing construct in state 2 with a tapered profile, accordingly to one or more embodiments.

The composite structural element described herein can have a variety of profiles. A non-limiting example is shown in FIG. 7, which demonstrates that the composite structural element 709 (pictured in state 2) can be designed to have a tapered profile. The composite structural element includes a bladder 707 with a tube 702 for connection with a fluid inflation/deflation source (not shown).

Figure 8A:
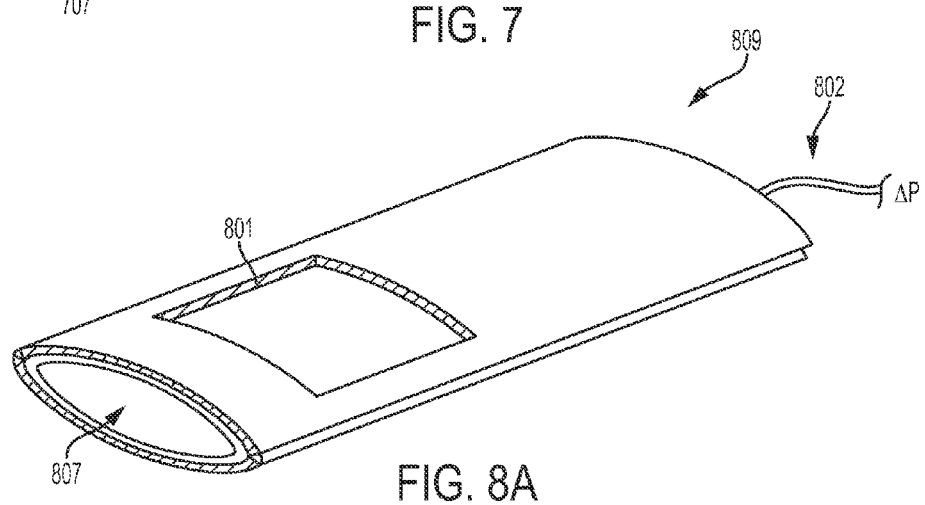
FIG. 8A: Illustrates an isometric view of a rigidizing construct in state 2 with a window in a layer that can provide viewing access into the bladder, accordingly to one or more embodiments.
Figure 8B:
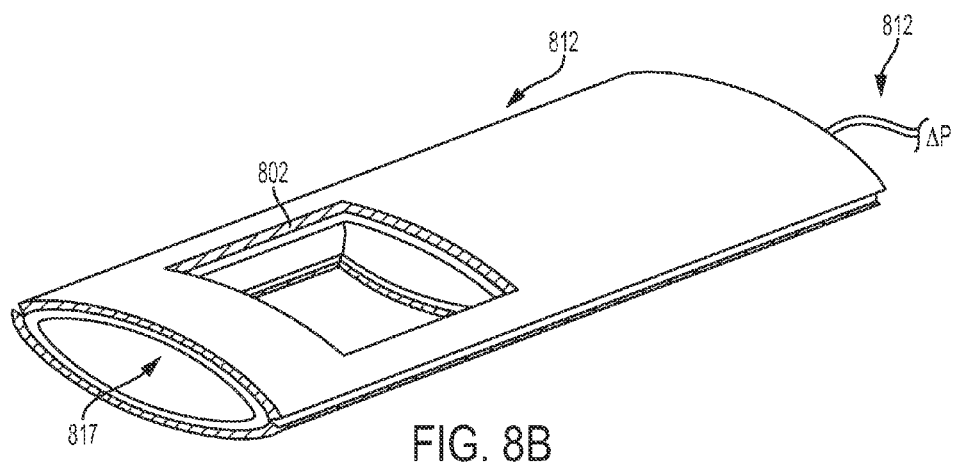
FIG. 8B: Illustrates an isometric view of a rigidizing construct in state 2 with a window that passes through the structure, accordingly to one or more embodiments.

In some embodiments, at least part of the laminate layers and/or the bladder can be made of transparent material thus enabling viewing access into the inside of the bladder. For instance, FIG. 8A illustrates a design in which a composite structural element 809 includes a window 801 in the layer which can provide viewing access into the bladder 807 (assuming the bladder is made of a transparent material), which is connected with a tube 802 for connection with a fluid inflation/deflation source (not shown). In other embodiments, the composite structural element can have one or more openings to allow a channel to pass through the composite structural element. For instance, FIG. 8B illustrates a design of a composite structural element 819 in which a window 802 in the material layers and the bladder permit objects to pass through the structure. The bladder 817 is similarly connected to a tube 812 which is configured for connection with a fluid inflation/deflation source (not shown). This can also be used as a cavity for holding objects (e.g. pumps, valves, batteries, specimens, etc.), especially if one of the layers is left intact to act as the floor of the cavity.

Figure 9A:
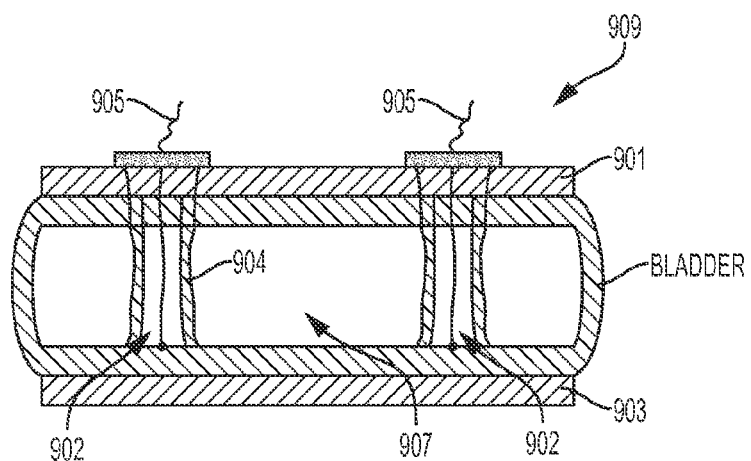
FIG. 9A: Presents a cross-section view of a rigidizing construct in state 2 with adjustable length internal reinforcements, accordingly to one or more embodiments.

In some embodiments, the composite structural element described herein can have internal reinforcement with adjustable length to adjust the curvature of the laminate layer and in turn the stiffness of the whole element. For instance, FIG. 9A demonstrates an extension of the internal reinforcements presented in FIGS. 3A-B and the cavity in FIG. 8B. In this scenario, a composite structural element 909 includes material or laminate layers 901 and 903, and a bladder 907 disposed in between the laminate layers. Two cavities 902 span the distance between the two laminate layers 901 and 903. Each cavity has a cavity wall 904 and inside these cavities is an adjustable length internal reinforcement 905. Non-limiting examples of the internal reinforcement 905 include a cable, shape memory alloy, and soft actuator (e.g. Mckibben actuator or a linear extending actuator). The adjustable length internal reinforcement could be used to adjust the spacing of the layers actively (by a user's adjustment or other mechanical means) or passively (by its default length) and therefore adjust the stiffness of the structure. In some embodiments, the internal reinforcement 905 can also permanently rigidize using methods described earlier. In this scenario, the pressurized fluid is used to define the shape of the composite structural element, and the permanent rigidizing methods irreversibly set or lock-in the shape of the laminate layers and the internal reinforcements.

Figure 9B:
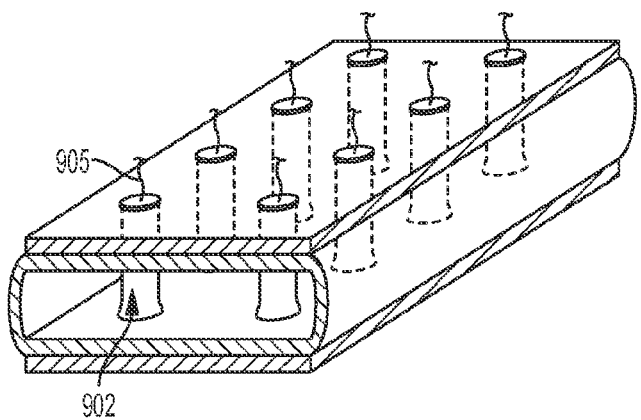
FIG. 9B: Presents an isometric cross-section view of the rigidizing construct with adjustable length internal reinforcements, accordingly to one or more embodiments.
Figure 9C:
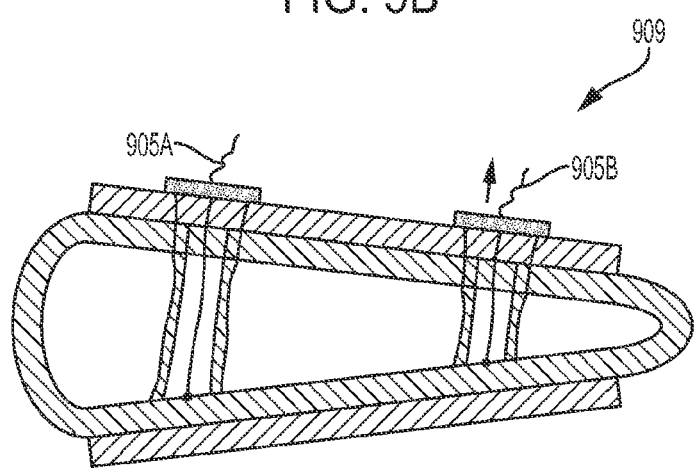
FIG. 9C: Presents a cross-section view of a rigidizing construct with adjustable length internal reinforcements where one of the reinforcements is shorter than the other, accordingly to one or more embodiments.

FIG. 9B illustrates an isometric cross-section view of the rigidizing composite structural element 909 with adjustable length internal reinforcements 905 in the cavity 902. In some embodiments, the adjustable length internal reinforcements 905 can be individually controlled or controlled in sections. Thus, sections of the internal reinforcements can be adjusted independently to result in a change in the shape or angle of the overall structure. For instance, FIG. 9C illustrates a cross-section view of the rigidizing composite structural element 909 where an internal reinforcement 905B is adjusted to a shorter length than a neighboring internal reinforcement 905A, causing the layers to change angle relative to one another. In some embodiments, this design can be used to adjust the airfoil of a wing or propeller. In other embodiments, this design can be used to adjust the angle of a photovoltaic relative to the sun's position.

Figure 10:
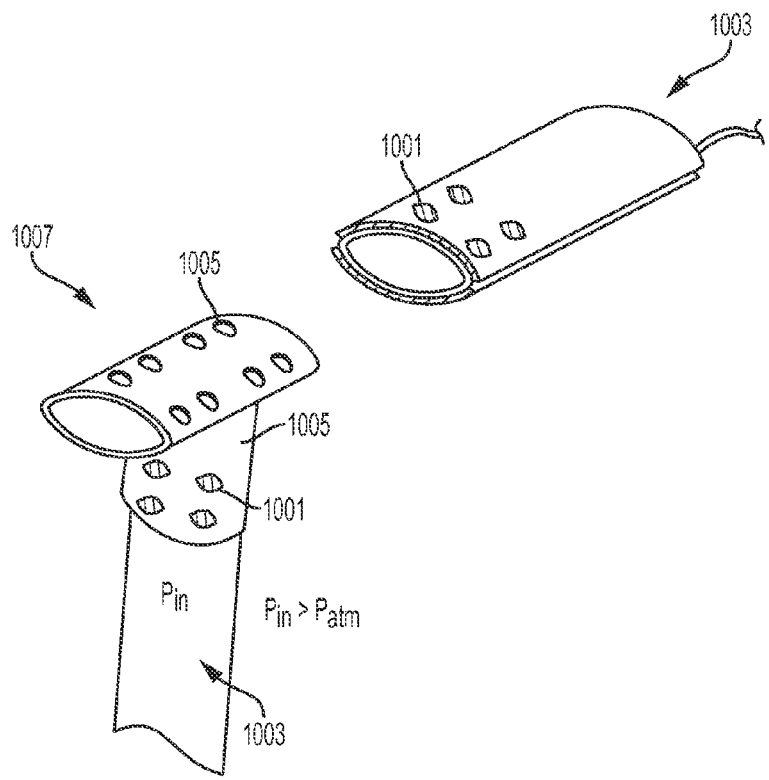
FIG. 10: Depicts an isometric view of a method by which rigidizing elements can be connected to construct larger structures, accordingly to one or more embodiments.

In some embodiments, an array of the composite structural elements is described, wherein the array includes two or more composite structural elements each according to any of the embodiments disclosed herein. As shown in FIG. 10, two rigidizing composite structural elements are connected to construct larger structures (FIG. 10). In this embodiment, there are raised features 1001 on the surface of the composite structural elements 1003 which match to pockets 1005 in the wall of the T-shape socket connector 1007. When the element 1003 is pressurized, it fills the inside volume of the socket 1007 to create a friction connection. The raised features 1001 may also fill into the pockets 1005 to increase the strength of the connection with a geometric constraint.

In some other embodiments, the socket and ends of the rigidizing element are made of rigid material such that they are connected by means of mechanical locking (e.g. snap together, threads, magnets, etc.) or chemical connection (e.g.

glue) (not shown). In some other embodiments, hydraulic or pneumatic connectors can be incorporated into the sockets and ends of the rigidizing elements. In this way, when rigidizing elements are connected to the sockets, pressurized fluid can travel from one rigidizing element to the other. This enables multiple rigidizing elements or an entire structure to be activated by one or more power sources. Further, these connectors may come in normally closed state so that the free end of a rigidizing element or empty socket does not release pressurized fluid. This construction strategy enables rigidizing elements to be added or removed from the structure as requirements change. The flexible nature of the rigidizing element in state 1 is especially useful when the element must be navigated around other rigidized elements in a dense structure such as in a lattice structure.

Figure 11:
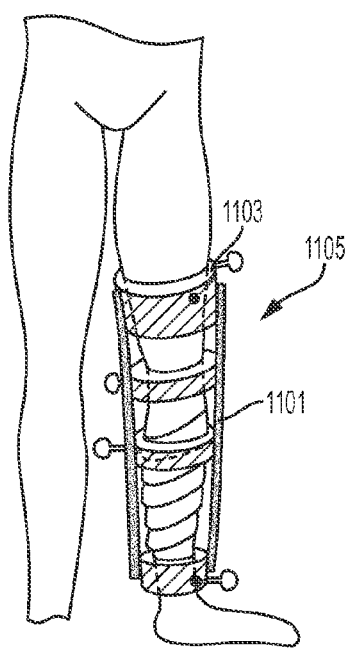
FIG. 11: Presents an application where a rigidizing beam can be integrated into a splint, accordingly to one or more embodiments.

In another embodiment, the composite structural element, e.g., a rigidized beam, can be used as part of a splint for a patient in need thereof. For instance, FIG. 11 illustrates an application where a rigidized composite structural element 1101 is integrated into a splint 1105. In some embodiments, the composite structural element 1101 bridges the gap between collars 1103 to align and stabilize the limb, and provide open wound access. The described application is for the leg of a patient, but can be extended to other parts of the body including wrists, arms, femurs, and so forth.

Figure 12A:
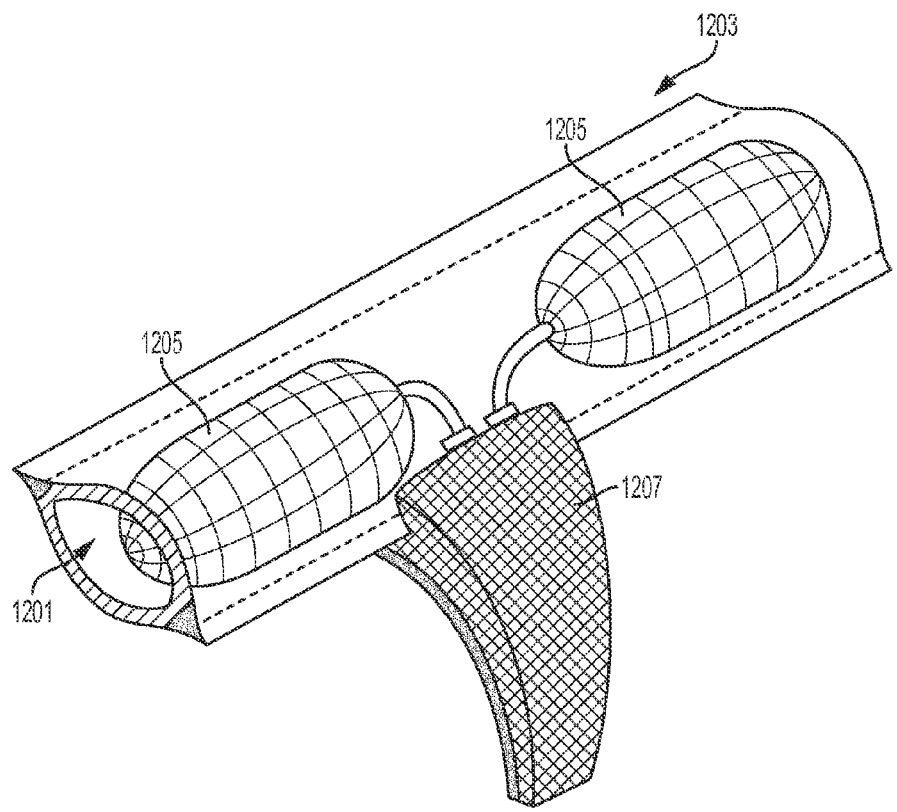
FIG. 12A: Presents an isometric view where the rigidizing beam can serve as a housing and support structure for system components, accordingly to one or more embodiments.

In yet other embodiments, the composite structural element, e.g., a rigidized beam, can act as a housing and support structure for system components. For instance, FIG. 12A depicts the composite structural element, e.g., a rigidized beam, as a housing and support structure for system components. In these embodiments, composite structural element 1203 comprises a bladder 1201 which houses high-pressure accumulators 1205 and/or other soft pneumatic distribution elements (tubes, junctions, check valves, flap valves, etc.). These components can be distributed within the inflated construct of element 1203 to serve as an infrastructure for external system components (e.g. soft actuators 1207 attached to the composite structural element 1203). For example, there can be multiple pneumatic or hydraulic connectors on the surface of the beam with requisite routing of tubes in the bladder.

Figure 12B:
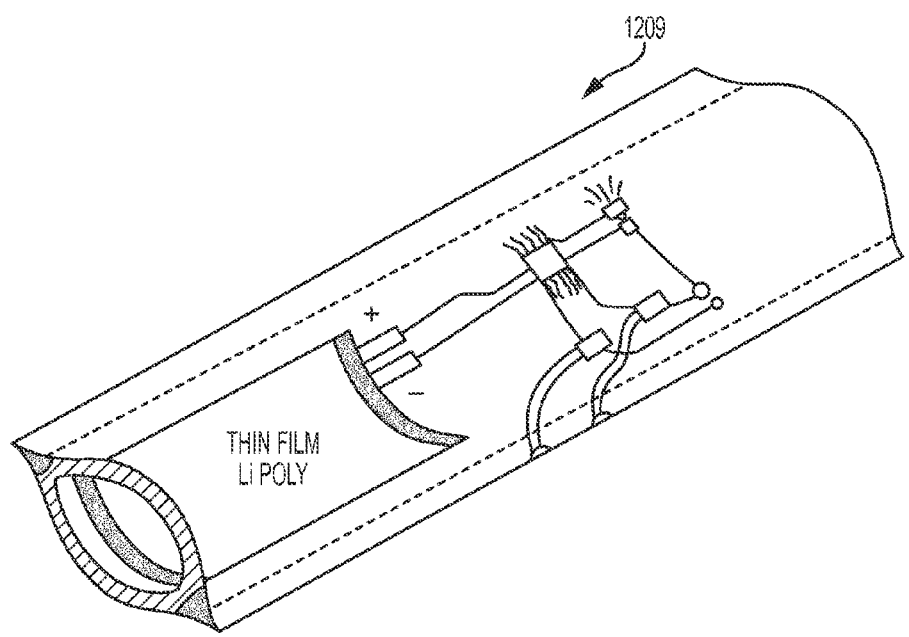
FIG. 12B: Presents an isometric view of other system components that can be integrated into the inner structure of the beam or its laminate layer(s), accordingly to one or more embodiments.

In still other embodiments, other system components can be integrated into the inner structure of the composite structural element or its laminate layer(s). For instance, FIG. 12B depicts other system components that can be integrated into the inner structure of the composite structural element 1209 or its laminate layer(s). Non-limiting examples of the system components include thin film electrical batteries, resistive heating elements, circuitry, strain sensors, electro-pneumatic valves and transducers, lighting, resistive force sensors, inertial sensors, and other sensing or electro-mechanical elements. In other embodiments, one of the laminate layers of the composite structural element comprises a lithium polymer battery.

Figure 13A:
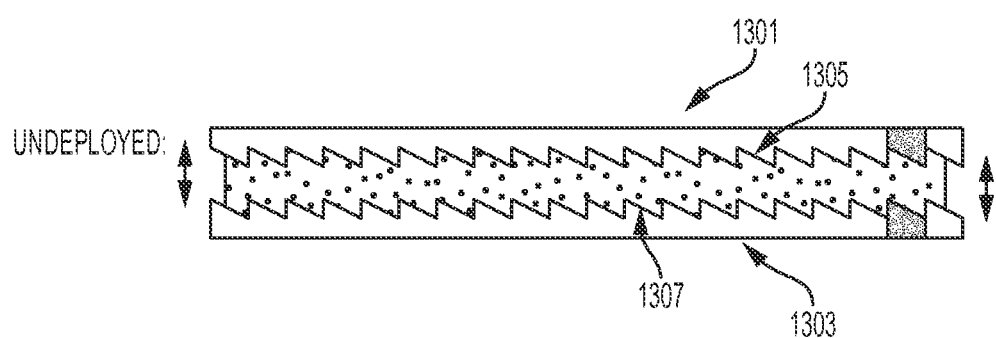
FIG. 13A: Presents a side view of laminates with opposing ratcheting teeth, accordingly to one or more embodiments.
Figure 13B:
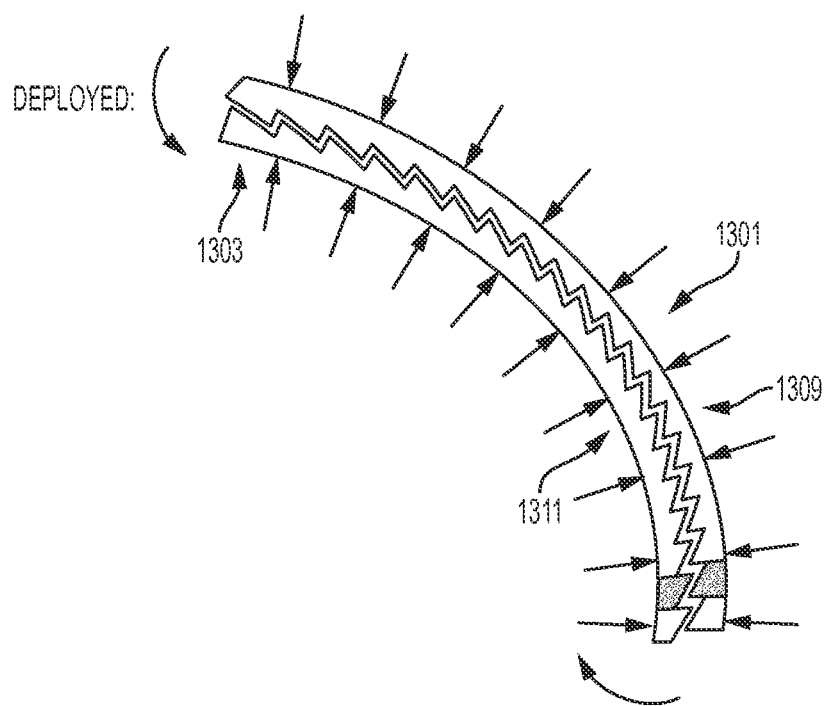
FIG. 13B shows that the ratcheting teeth can impart directional bending preferences after activation of the bladder by pressure or application of vacuum to the laminates, accordingly to one or more embodiments.

In some embodiments, the two adjacent laminate layers can be bounded together or freely separable. In a further embodiment, the two adjacent laminate layers can include a mechanism to result in preference to one bending direction over another. In some embodiments, the surfaces of the two adjacent first material layers or the two adjacent second material layers are textured to create high friction between the first material layers or between the second material layers, respectively, when the bladder is inflated. For instance, FIG. 13A shows two adjacent material or laminate layers 1301 and 1303 each with a set of opposing ratcheting teeth, 1305 and 1307, on their facing surfaces, respectively. This design is used as a laminate texture to impart directional bending effects after pressurization of the bladder or application of vacuum to the laminates (FIG. 13B). Given that the teeth is small enough with respect to the beam's thickness, bending of the construct could be easily achieved in the direction where each tooth's interface is sloped (direction indicated by arrow 1311). In the opposing direction (direction indicated by arrow 1309), bending would be strongly opposed by interlocking of the laminate layers against each flat tooth edge.

In another embodiment, a pressurized bladder can drive a metal sheet from a coiled state to a linear beam. In addition, an inflator can be used to buckle a linear beam in order for it to retain its linear form in the absence of the further application of force from the pneumatic system. For instance, FIG. 14A is a side view of the device in its coiled state before pneumatic actuation, which shows a rectangular bladder can be affixed to the surface of the coiled metal sheet. FIG. 14B is a side view of the device in its inflated state. The metal sheet is elongated due to the inflation of the bladder which because of its shape will naturally unfurl to a linear form. Finally, the combination of the metal sheet and bladder can be constructed such that the bladder buckles the sheet. This effect is illustrated in FIGS. 14C-14E. FIG. 14C shows a cross-section view of the device, taken perpendicular to its length, before inflation. Before inflation, the metal sheet is flat. Next, the bladder is inflated which initially bows the metal sheet until the sheet is driven through a buckling transition, as illustrated in FIG. 14D. This buckling transition allows the metal sheet to remain in its coiled state without any need for further application of pressure. Finally, the bladder can be further inflated, as shown in FIG. 14E, in order to provide additional rigidity to the bean though this step is not required to maintain the elongation of the sheet.

In yet another aspect, a composite structural element array is described, including two or more composite structural elements each according to any of the embodiments described herein. The two or more composite structural elements may be combined or connected, reversibly or irreversibly in series, parallel, or at an angle. In some embodiments, each of the composite structural elements is connected to the same material infusion or vacuum source. In other embodiments, at least two of the composite structural elements are connected to different material infusion or vacuum sources.

In yet another aspect, a device is described, including a composite structural element of any one of the embodiments described herein, wherein the device is selected from the group consisting of a splint, a wing structure, a load bearing scaffold, a shelter, a bullet proof vest, a communication tower, bridge and a truss. In certain embodiments, the splint is a splint for wrist, arm, leg, or femur.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention.

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation.

Examples of specific implementations and applications are provided primarily for illustrative purposes.

What is claimed is:

1. A composite structural element, comprising:
   a first laminate layer comprising a plurality of first material layers;
   a second laminate layer comprising a plurality of second material layers, wherein at least one of the first and second laminate layers is housed in a flexible sleeve; and
   an inflatable bladder configured for connection with a material infusion or vacuum source and disposed between the first and second laminate layers;
   wherein the composite structural element is configured to rigidize when the bladder is inflated.

2. The composite structural element of claim 1, wherein each of the first material layers is made from a material the same as any other first material layers or different from at least one other first material layer.

3. The composite structural element of claim 1, wherein each of the second material layers is made from a material the same as any other second material layers or different from at least one other second material layer.

4. The composite structural element of claim 1, wherein the bladder has a membrane and the first and/or second material layers adjacent to the bladder are bounded to the bladder's membrane.

5. The composite structural element of claim 1, wherein one of the first material layers and one of the second material layers are sealed together to form the membrane of the bladder.

6. The composite structural element of claim 1, wherein the first and second laminate layers are configured to become more rigid when the bladder is pressurized.

7. The composite structural element of claim 1, wherein the first and/or second laminate layers are configured to curve when the bladder is pressured.

8. The composite structural element of claim 1, wherein the distance between the first and second laminate layers is configured to increase when the bladder is pressurized.

9. The composite structural element of claim 1, wherein the distance between the first and second laminate layers is configured to increase and the first and/or second laminate layers are configured to curve when the bladder is pressured.

10. The composite structural element of claim 1, wherein the first and second laminate layers each independently comprise 2, 3, 4, 5, 6, 7, or more first or second material layers, respectively.

11. The composite structural element of claim 1, wherein the space between the first material layers or the second material layers is configured for connection with a vacuum source.

12. The composite structural element of claim 1, wherein the facing surfaces of the two adjacent first material layers or the two adjacent second material layers are textured to create high friction between the first material layers or between the second material layers, respectively, when the bladder is inflated.

13. The composite structural element of claim 1, wherein the first or second material layers are rubberized to create high friction between the material layers when the bladder is infused.

14. The composite structural element of claim 1, wherein the two adjacent first or second material layers have patterned surfaces to create a mechanically interlocked bond between laminates when the bladder is infused.

15. The composite structural element of claim 1, wherein the two facing surfaces of the adjacent first material layers or the adjacent second material layers each comprises a set of opposing ratcheting teeth configured to interlock to impart directional bending effects after the bladder is infused.

16. The composite structural element of claim 1, wherein the two adjacent first or second material layers are bounded together.

17. The composite structural element of claim 1, wherein the two adjacent first material layers or the second material layers freely slide pass one another.

18. The composite structural element of claim 1, wherein the composite structural element is configured to de-rigidize when the bladder is deflated.

19. The composite structural element of claim 1, wherein the first or second laminate layer comprises integrated electronic circuitry.

20. The composite structural element of claim 1, wherein the first and/or second laminate layers are sealed in the sleeve and the sleeve is configured for connection with a vacuum resin infusion system.

21. The composite structural element of claim 1, wherein both the first and second laminate layers and the bladder are housed in a sleeve.

22. The composite structural element of claim 1, wherein the composite structural element is capable of being rolled or folded.

23. The composite structural element of claim 1, wherein the first and/or second material layer further comprises one or more openings configured to allow viewing access into the bladder.

24. The composite structural element of claim 1, wherein the composite structural element has a tapered geometry.

25. The composite structural element of claim 1, wherein the first or second laminate layers are made from puncture-resistant and/or bulletproof materials.

26. The composite structural element of claim 1, wherein at least one of the first and second laminate layers is housed in a sleeve containing shear thickening fluids.

27. The composite structural element of claim 1, wherein the structural element has a rigid body when the bladder is infused.

28. The composite structural element of claim 1, wherein the composite structural element permanently rigidizes when the bladder is inflated.

29. The composite structural element of claim 28, wherein at least one material layer comprises polymerizable monomers susceptible to UV polymerization.

30. The composite structural element of claim 28, wherein the bladder is configured for connection with a resin infusion source or a foam inflation source.

31. The composite structural element of claim 28, wherein the material layer comprises pre-preg composite materials configured to be cured through chemical, radiant, or electrical means.

32. The composite structural element of claim 1, wherein the first and/or second laminate layers are sealed in the sleeve and the sleeve is configured for connection with a vacuum source.

33. The composite structural element of claim 32, wherein the bladder is configured to be infused before the sealed sleeve is subjected to the vacuum.

34. The composite structural element of claim 1, wherein the bladder houses one or more system components.

35. The composite structural element of claim 34, wherein the system component is a soft actuator.

36. The composite structural element of claim 1, wherein the first and/or second material layer further comprises one or more openings passing through the bladder and the first and/or second material layer.

37. The composite structural element of claim 36, wherein the opening is configured to house one or more additional system components or materials.

38. A device comprising a composite structural element of claim 1, wherein the device is selected from the group consisting of a splint, a wing structure, a load bearing scaffold, a shelter, a bullet proof structure, a communication tower, bridge and a truss.

39. The device of claim 38, wherein the splint is a splint for wrist, arm, leg, or femur.

40. A composite structural element comprising:
a first laminate layer comprising a plurality of first material layers;
a second laminate layer comprising a plurality of second material layers;
an inflatable bladder configured for connection with a material infusion or vacuum source and disposed between the first and second laminate layers; and
one or more internal reinforcements in the bladder spanning between the first and second laminate layers and configured to define the separation distance between the first and the second laminate layers when the bladder is inflated,
wherein the composite structural element is configured to rigidize when the bladder is inflated.

41. The composite structural element of claim 40, wherein the separation distance may be adjusted actively or passively.

42. The composite structural element of claim 40, wherein the composite structural element comprises a plurality of the reinforcements configured to be independently adjusted or adjusted as a group.

43. A composite structural element array, comprising two or more composite structural elements each according to the composite structural elements of claim 1, combined or connected, reversibly or irreversibly in series, parallel, or at an angle.

44. The composite structural element array of claim 43, wherein each of the composite structural elements is connected to the same material infusion or vacuum source.

45. The composite structural element array of claim 43, wherein at least two of the composite structural elements are connected to different material infusion or vacuum sources.

* * * * *